(12) United States Patent
Lin

(10) Patent No.: US 11,612,730 B1
(45) Date of Patent: Mar. 28, 2023

(54) ALL-IN-ONE ARTERIAL ACCESS AND CLOSURE SYSTEM (ACS)

(71) Applicant: LI-MEI LIN, M.D. MEDICAL MANAGEMENT CORPORATION, Tucson, AZ (US)

(72) Inventor: Li-Mei Lin, Tucson, AZ (US)

(73) Assignee: LI-MEI LIN, M.D. MEDICAL MANAGEMENT CORPORATION, Tucson, AZ (US)

( * ) Notice: Subject to any disclaimer, the term of this patent is extended or adjusted under 35 U.S.C. 154(b) by 477 days.

(21) Appl. No.: 16/831,393

(22) Filed: Mar. 26, 2020

Related U.S. Application Data

(60) Provisional application No. 62/823,839, filed on Mar. 26, 2019.

(51) Int. Cl.
*A61M 39/02* (2006.01)
*A61F 2/95* (2013.01)
(Continued)

(52) U.S. Cl.
CPC ......... *A61M 39/0247* (2013.01); *A61B 34/20* (2016.02); *A61F 2/95* (2013.01); *A61M 5/14* (2013.01); *A61M 25/06* (2013.01); *A61B 17/06166* (2013.01); *A61B 2017/00584* (2013.01); *A61B 2017/00778* (2013.01); *A61B 2017/00867* (2013.01);
(Continued)

(58) Field of Classification Search
CPC ...... A61B 17/0057; A61B 2017/00575; A61B 2017/00579; A61B 2017/00584; A61B 2017/00588; A61B 2017/00592; A61B 2017/00597; A61B 2017/00601; A61B 2017/00606; A61B 2017/0061; A61B 2017/00615; A61B 2017/00619; A61B 2017/00623; A61B 2017/00628; A61B 2017/00637; A61B 2017/00646; A61B 2017/0065; A61B 2017/00654; A61B 2017/00668; A61B 2017/00676
See application file for complete search history.

(56) References Cited

U.S. PATENT DOCUMENTS 6,391,048 B1    5/2002 Ginn et al.
6,461,364 B1   10/2002 Ginn et al.
(Continued)

OTHER PUBLICATIONS

Rao et al. Arterial access and arteriotomy site closure devises. Nature Reviews Cardiology. Nov. 2016, 641-650, vol. 13. Macmillian Publishers Limited.

*Primary Examiner* — Thomas McEvoy
(74) *Attorney, Agent, or Firm* — Nguyen Tarbet LLC

(57) ABSTRACT

The present invention features an all-in-one system for vascular access and closure. In particular, this invention features systems and methods for forming holes in blood vessels and rapidly closing these vessel holes using an all-in-one system. For example, an arterial access and closure port system is disclosed herein to provide fail-safe percutaneous entry and exit into any artery, particularly useful for high flow and high pressure arteries such as the carotid artery. The present invention is a single system that forms and closes vascular holes and can be used for percutaneous arterial access with interventional radiology, interventional cardiology, neuro-intervention, endovascular surgery, and endovascular neurosurgery.

6 Claims, 11 Drawing Sheets

(51) Int. Cl.
*A61M 5/14* (2006.01)
*A61B 34/20* (2016.01)
*A61M 25/06* (2006.01)
*A61B 17/06* (2006.01)
*A61B 17/34* (2006.01)
*A61B 17/00* (2006.01)
*A61B 90/00* (2016.01)
*A61M 25/10* (2013.01)

(52) U.S. Cl.
CPC ............... *A61B 2017/3413* (2013.01); *A61B 2034/2063* (2016.02); *A61B 2090/065* (2016.02); *A61B 2090/376* (2016.02); *A61B 2090/3925* (2016.02); *A61B 2090/3966* (2016.02); *A61M 25/10* (2013.01); *A61M 2039/0258* (2013.01); *A61M 2039/0273* (2013.01); *A61M 2039/0276* (2013.01)

(56) References Cited

U.S. PATENT DOCUMENTS

| | | | |
|---|---|---|---|
| 7,025,776 B1 | 4/2006 | Houser et al. | |
| 7,850,654 B2 | 12/2010 | Belhe et al. | |
| 9,561,345 B2 | 2/2017 | Garrison et al. | |
| 10,039,535 B2 | 8/2018 | Ginn et al. | |
| 2007/0083232 A1 | 4/2007 | Lee | |
| 2007/0149880 A1* | 6/2007 | Willis | A61N 7/02 600/471 |
| 2009/0171387 A1 | 7/2009 | Pipenhagen et al. | |
| 2010/0204684 A1 | 8/2010 | Garrison et al. | |
| 2010/0217086 A1* | 8/2010 | Deshmukh | A61B 17/0218 600/205 |
| 2010/0228269 A1 | 9/2010 | Garrison et al. | |
| 2013/0197621 A1 | 8/2013 | Ryan et al. | |
| 2014/0025103 A1* | 1/2014 | Hundertmark | A61B 17/0057 606/213 |
| 2019/0015086 A1* | 1/2019 | Blumenthal | A61B 17/0057 |

* cited by examiner

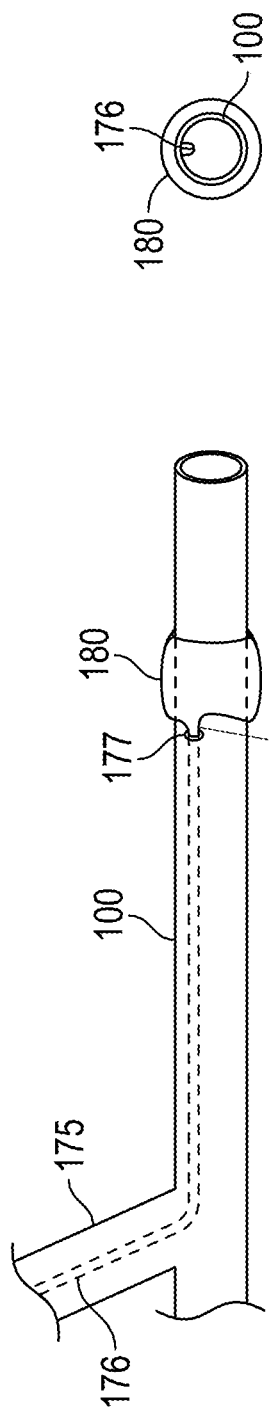
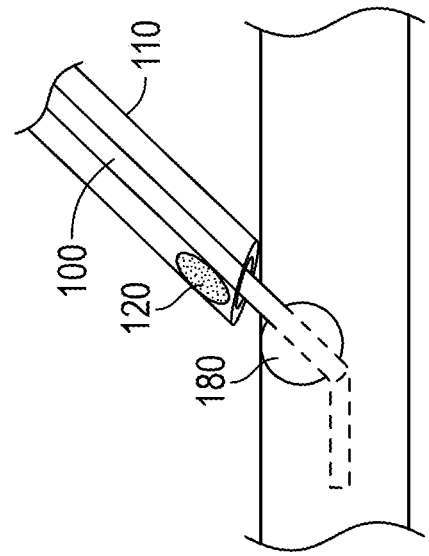
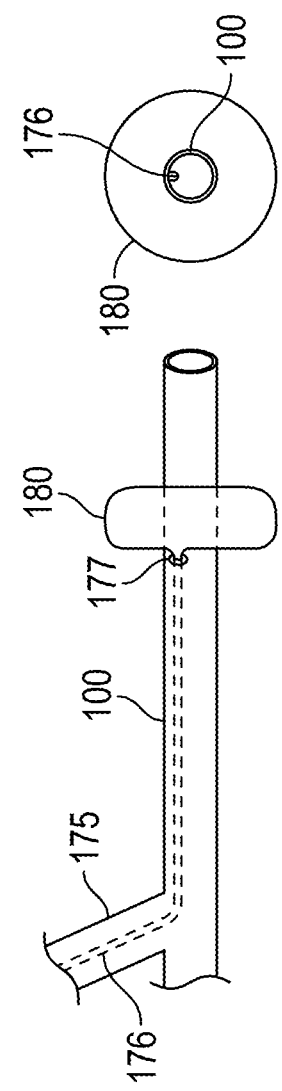

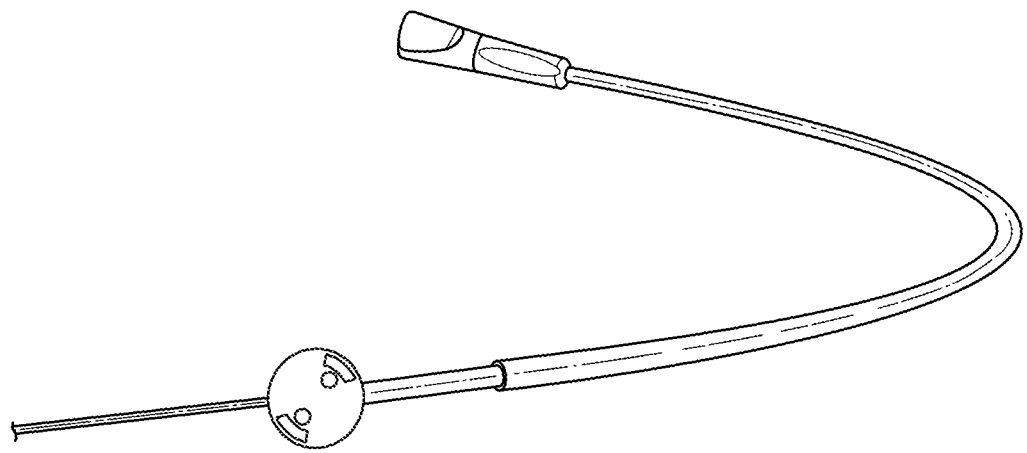
FIG. 7C
(Prior Art)
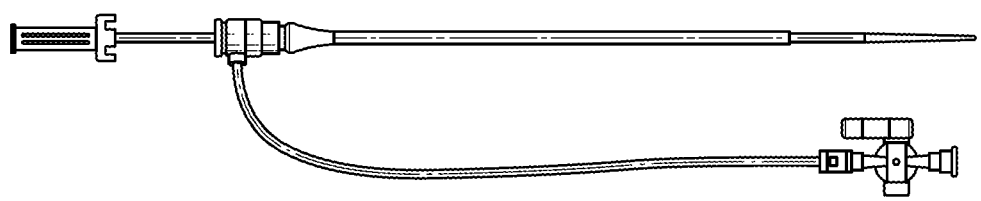
FIG. 8A
(Prior Art)
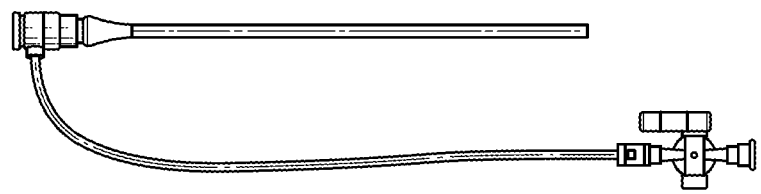
FIG. 8B
(Prior Art)

ALL-IN-ONE ARTERIAL ACCESS AND CLOSURE SYSTEM (ACS)

CROSS-REFERENCES TO RELATED APPLICATIONS

This application is a non-provisional and claims benefit of U.S. Provisional Application No. 62/823,839 filed Mar. 26, 2019, the specification of which is incorporated herein in its entirety by reference.

FIELD OF THE INVENTION

The present invention features an all-in-one system for vascular access and closure, an access and closure system (ACS). In particular, this invention features systems and methods for forming holes in blood vessels and rapidly closing these vessel holes using an all-in-one system. For example, an arterial access and closure port system is disclosed herein to provide fail-safe percutaneous entry and exit into any artery, particularly useful for high flow and high pressure arteries such as the carotid artery. The present invention is a single system that forms and closes vascular holes and can be used for percutaneous arterial access with interventional radiology, interventional cardiology, neuro-intervention, endovascular surgery, and endovascular neurosurgery.

BACKGROUND OF THE INVENTION

Stroke care has improved in the last three years after multiple clinical trials demonstrated the ability to reverse stroke symptoms with the mechanical removal of a clot via endovascular means similar to cardiac catheters for heart attacks. This has brought to the forefront the need for speed in revascularization. These cases are routinely performed via femoral artery access, with some interest in this past year for radial artery access. The quickest direct route is via the carotid artery in the neck, providing time-saving which translates to faster revascularization and improved patient outcome. However, there is much hesitation and fear with direct carotid access given lack of highly reliable closure devices for high flow arteries.

Limitations and risks are associated with current vascular closure solutions. For example, a manual pressure method takes time, ranging from 10 minutes to 45 minutes. Suture-mediated closure systems cinch the arterial opening with a suture (e.g., Perclose Proglide®, Starclose®) in FIG. 7A, which risks narrowing the artery. Another closure device shown in FIG. 7B leaves a footplate inside the artery up against the arterial opening (e.g., Angi-Seal™). This "endolumen" footplate risks clotting in artery or narrowing the artery. Another closure device shown in FIG. 7C provides a hemostasis sponge outside the arterial opening (e.g., Mynx®). This sponge has a 50% failure rate, making it an unreliable closure system. Due to the unreliability and risks of current closure solutions, there is a need for highly reliable, fail-safe arterial closure devices, particularly for a high flow artery such as the carotid arterial access/sheath.

BRIEF SUMMARY OF THE INVENTION

It is an objective of the present invention to provide systems and methods that allow for both vascular access or opening/entry and vascular closure in one system, as specified in the independent claims. Embodiments of the invention are given in the dependent claims. Embodiments of the present invention can be freely combined with each other if they are not mutually exclusive.

The present invention features an all-in-one system for forming and closing a hole in a blood vessel. For example, the same system is used for both gaining access to an artery (or opening or cutting an artery, arteriotomy) as well as for closing the arterial hole. In preferred embodiments, the system comprises a first tube, a second tube, and a closure mechanism. The first tube opens or creates a hole in the blood vessel and the second tube is concentric to and/or surrounds the first tube in a system configuration that allows the first tube not to facilitate the entry of the second tube into the vessel and refraining the second tube to be at or near the outer surface of the vessel. The second tube also effectuates the closure mechanism. The closure mechanism closes the opening or hole in the blood vessel formed by the first tube.

In some embodiments, the closure mechanism can be disposed in a space between the second tube and the first tube or disposed along the distal end of the second tube that surrounds the first tube, the second outer tube serving as an extra lumen access for a closure mechanism. The closure mechanism of the system can be delivered by this extra lumen access (a second lumen/access port) as shown in FIG. 1 or by a shorter outer tube surrounding the inner arterial sheath portion with a system provided in FIG. 2C. In some embodiments, the first tube aids in closing the opening or hole in the blood vessel after retraction. For example, after the closure mechanism is disposed over the opening or hole, a hemostatic foam may be injected through the first tube to aid the closure mechanism in sealing the opening or hole. In other embodiments, a closure balloon may be disposed at the distal end of the first tube in a deflated state. After the first tube is retracted and the closure mechanism is disposed over the opening or hole, the closure balloon may be inflated to apply pressure to the closure mechanism and aid in sealing the opening or hole.

In some embodiments, the all-in-one system further comprises a balloon inflation port that is integrated with the first tube. For example, the first tube may comprise a first lumen and a second lumen. The first lumen is configured to have a medical device (e.g., catheter, stent, balloon, therapeutic drug infusion, or wire) inserted therein, and the second lumen is fluidly coupled to the balloon inflation port. In one embodiment, an inflatable balloon is located at or near the distal end of the first tube and fluidly coupled to the balloon inflation port via the second lumen. The balloon is configured to be inflated for locating the hole in the vessel. In other embodiments, the distal ends (tips) of the inner tube and the outer tube may be radiodense for visibility under fluoroscopy or echogenic for visibility with ultrasound. In other embodiments, the tubes or the tips of each of the inner tube and the outer tube may be equipped with a pressure monitoring sensor and/or a flow monitoring sensor.

The closure mechanism may be applied through the use of a flexible hinge disposed at a distal end of the outer tube in a space between the outer tube and the inner tube. The closure mechanism may be disposed at an end of the flexible hinge. The inner tube when extended may hold the flexible hinge in a tension state, and the inner tube when retracted may cause the flexible hinge to move into a memory state. The movement into the memory state may cause the closure mechanism to be moved to cover the entry hole with enough force to detach the closure mechanism from the flexible hinge, such that removing the outer tube may leave the closure mechanism in an engaged position.

One of the unique and inventive technical features of the present invention is the all-in-one system, i.e., a single system, for both forming and closing a hole in a blood vessel. The system provides a single tube for creating a hole and entering a vessel (serving as an endolumen) integrated with another tube that does not enter the vessel and affords the closure mechanism to be at or near the hole, thereby allowing for rapid closure of the hole. Without wishing to limit the invention to any theory or mechanism, it is believed that the technical feature of the present invention advantageously provides for vascular entry and rapid vascular closure using the same system. None of the presently known prior references or work has the unique inventive technical feature of the present invention In addition, the system of the present invention includes an outer tube that is configured not to enter the vessel and remain outside the vessel wall. In some embodiments, the outer tube functions to close the access hole from the outer surface of the vessel without having to enter inside of the vessel. For example, the distal end of the outer tube is blunted so as not to puncture the vessel upon placement of the outer tube on the vessel. In other embodiments, the outer tube surrounds the inner tube, particularly at the distal end, providing a larger diameter of the system so that the outer tube cannot enter the vessel when the inner tube is inserted into the vessel.

There is a lack of understanding of where the vessel hole/entry is located using the prior art methodology. The present invention resolves this problem by integrating the access mechanism and closure mechanism into one system, thereby focusing on the importance of localizing the vessel hole/entry as well as the close proximity of the closure mechanism to the hole to provide a fail-safe reliable closure of the hole from outside of the vessel. For example, a balloon functionality near the distal tip of the inner tube can be used to locate the hole from inside the vessel and the distal tip of the outer tube (with a closure mechanism) that is used to locate the hole from outside the vessel, thus placing the vessel wall in between the two tubes, allowing the closure mechanism to be at or near the vessel hole to effectively close the hole.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 2A shows a representation of an inner tube of the present invention having a deflated balloon connected to an inflation tube.

FIG. 2B shows a representation of an inner tube of the present invention having an inflated balloon connected to the inflation tube.

FIG. 2C shows an embodiment of the vessel opening and closure system of the present invention incorporating the inflated balloon.

FIG. 7C shows the prior art, the Mynx® Vascular Closure Device, which provides a hemostasis sponge outside the arterial opening.

FIGS. 8A-8B show a prior art arterial sheath that consists of an inner introducer/dilator and an outer arterial sheath.

DETAILED DESCRIPTION OF THE INVENTION

Figure 1:
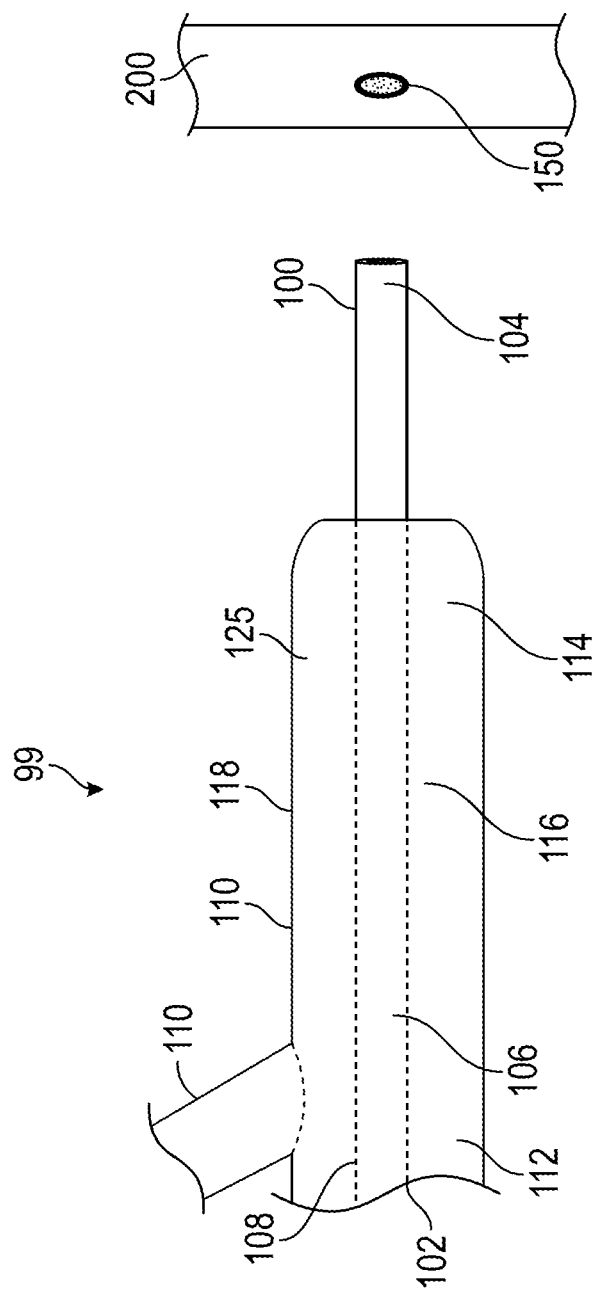
FIG. 1 shows a non-limiting example of an embodiment of the vessel opening and closure system of the present invention.

Following is a list of elements corresponding to a particular element referred to herein:
  99 all-in-one vessel opening/access and closing system
  100 first tube or inner tube
  102 first proximal end of first tube or inner tube
  104 first distal end of the first tube or inner tube
  106 first inner surface of first tube or inner tube
  108 first outer surface of first tube or inner tube
  110 second tube or outer tube
  112 second proximal end of second tube or outer tube
  114 second distal end of second tube or outer tube
  116 second inner surface of second outer tube
  118 second outer surface of second outer tube
  120 closure mechanism
  121 second closure mechanism
  122 released position of closure device
  124 enclosed position of closure device
  125 space between first tube and second tube
  126 engaged position of closure device
  130 detachment zone for closure device
  150 hole, entrance, or opening to the vessel
  175 balloon inflation port
  176 balloon inflation tube
  177 balloon inflation tube orifice
  180 inflated balloon (used to locate vessel hole from inside the vessel)
  199 all-in-one vessel opening/access and closing system with flexible hinge
  200 vessel
  210 outer surface of the vessel
  300 flexible hinge
  302 first flexible hinge closure holder
  303 second flexible hinge closure holder
  304 first flexible hinge arm
  305 second flexible hinge arm
  312 flexible hinge distal end
  313 second flexible hinge distal end 314 flexible hinge proximal end
315 second flexible hinge proximal end
1302 plunger
1312 hammer
1320 dislodging chemical
1330 dissolving chemical As used herein, the term "vessel" refers to a duct, canal, or other tube that contains or conveys a body fluid. For example, a blood vessel, artery, or vein.

As used herein, the term "lumen" refers to the inside space of a tubular structure, such as a cannula or an artery. The term "lumen" may also be used to describe the inside space of a cellular component or structure.

Referring now to FIGS. 1-8B, the present invention features an all-in-one vascular opening/access and dosing system and a method of using such a system for opening and closing a hole in a blood vessel.

In preferred embodiments, the present invention features an all-in-one system (99) for forming and closing a hole (150) in a blood vessel (200). A non-limiting example (shown in FIG. 1) comprises a single device that is used for gaining access (e.g., by forming a hole) to an artery or a vein (e.g., to insert a catheter or stent) and then for closing the vascular entry point or hole (150). The system comprises a first tube (100), a second tube (110), and a closure mechanism (120). The first tube (100) forms the hole (150) in the blood vessel (200); the second tube (110) is in a position or space relative to the first tube (100) to effectuate the closure mechanism (120), e.g., the second tube (110) is concentric to the first tube (100) and/or the second tube (110) surrounds the first tube (100) allowing the closure mechanism (120) to be at or near the hole (150) in the vessel (200) to effectively dose the hole or opening (150) to the blood vessel (200). The first tube (100) may be longer than the second tube (110), and the difference between a length of the first tube (100) and a length of the second tube (110) may vary depending on the distance between a skin layer and the vessel (200). In some embodiments, the first tube (100) may comprise a different material than a material of the second tube (110). The material of the first tube (100) may be more flexible than the material of the second tube (110). The first tube (100) may be marked so as to easily determine how far the first tube (100) has been extended into the vessel (200).

The closure mechanism (120) can be effectuated by the second tube (110). Non-limiting examples may comprise that the closure mechanism (120) is disposed in a space (125) between the second tube (110) and the first tube (100) or the closure mechanism (120) is a detachable closure device disposed along the distal end (114) of the second tube (110), which surrounds the first tube (100), in a position to be at or near the hole (150) of the blood vessel (200). The closure mechanism (120) is a closing device or a substance that effectively covers, seals, or closes the hole (150) in the blood vessel (200) in a fail-safe manner that prevents re-opening of the hole (150). The closure mechanism (120) may be selected from a group consisting of a metal clip, a hemostatic foam, a suture, a biodegradable patch, and an adhesive gel.

In some embodiments, the system of the present invention may further feature a balloon inflation port (175) that can be connected to or is part of or integrated with the first tube (100) as shown in FIGS. 2A-2B. The first tube then has two lumens, an inner lumen where a medical device (e.g., catheters, stents, wires, therapeutic drugs, etc) can be inserted and a second lumen with a balloon inflation tube (176) that is fluidly coupled to the balloon inflation port (175). The balloon inflation tube (176) may travel from an interior space enclosed by the inner tube (100) to the inflatable balloon (180) through an inflation tube orifice (177). The inflatable balloon (180) is located at or near the distal end (104) of the first tube and fluidly coupled to the balloon inflation port (175) via the balloon inflation tube (176). The balloon (180) is configured to be inflated via the balloon inflation tube (176) and used to locate the hole (150) in the blood vessel (200) (FIG. 2C). In some embodiments, either the inner tube or outer tube can be used to determine whether or not the closure mechanism (120) was successfully placed, as blood will begin escaping through either tube if the closure mechanism (120) failed to close the vessel (200).

The present invention further features a percutaneous blood vessel entry and closure system. The system is a single, all-in-one, system (99) that (1) forms a hole (150) in an artery (200) or vein (200) and (2) closes the hole (150) in the artery or vein (200). The system comprises a first tube (100) for forming or creating a hole (150) in the blood vessel (200), a second tube (110) surrounding the first tube (100), and a closure device (120). As shown in FIG. 6A-6F, a needle is initially inserted into the vessel (200), and a wire is directed through the needle to maintain access to the interior of the vessel (200) as the needle is removed. Upon removal of the needle, the all-in-one system (99), further comprising a dilator removably disposed in the first tube (100), is inserted into the vessel (200) using the wire as a guide. The wire is then retracted from the vessel (200). The dilator is then removed from the vessel (200), leaving the first tube (100) with interior access to the vessel (200) through the hole (150). The second tube (110), which is concentric to and/or surrounds the first tube (100) has a distal end (114) that is tapered, has a tip, or has a detachable closing mechanism (120) juxtaposed along its end. The distal end of the second tube (114) can be inserted through the skin to provide the same percutaneous access location to the blood vessel (200) as the first tube (100) and to be disposed at or near the hole (150) of the vessel (200) from outside the vessel (200). In some embodiments, the closure mechanism (120) is effectuated in a space (125) between the first (100) and second tubes (110). The closure mechanism (120) closes the opening or hole (150) to the blood vessel (200) that was created by the distal end of the first tube (104). The difference in diameter between the hole (150) created by the first tube (100) and the second tube (110) creates a rim for the closure mechanism (120) to rest over.

In some embodiments, the tips of the inner tube (100) and the outer tube (110) are also radiodense for visibility under fluoroscopy or echogenic for visibility with ultrasound. In other embodiments, the tubes and/or the tips of each of the inner tube (100) and the outer tube (110) are equipped with a pressure monitoring sensor and/or a flow monitoring sensor.

Figure 3A:
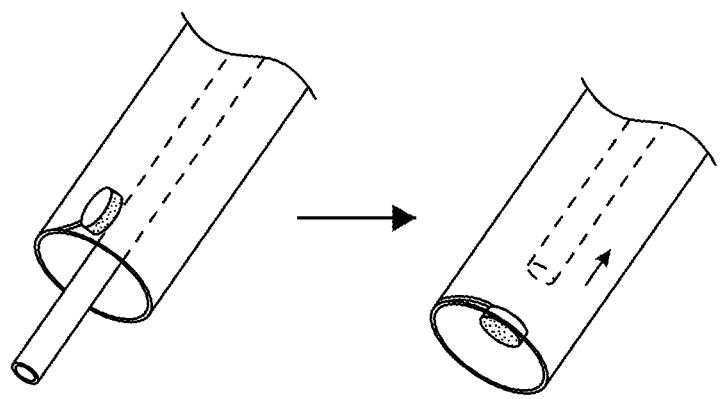
FIG. 3A shows a representation of the vessel opening and closure system with one closure mechanism attached to a flexible hinge.
Figure 3B:
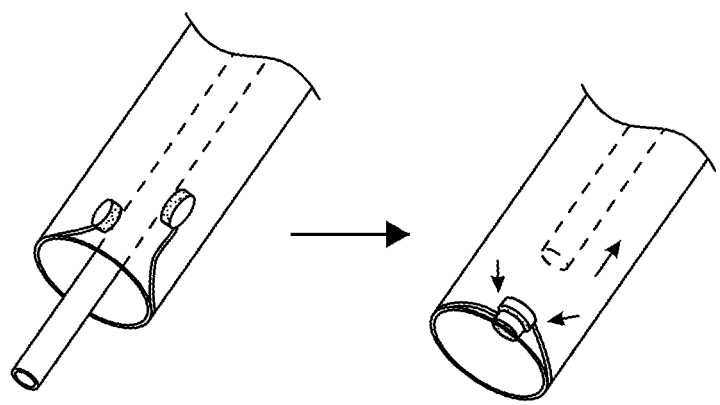
FIG. 3B shows a representation of the vessel opening and closure system with two closure mechanisms attached to two flexible hinges.
Figure 4A:
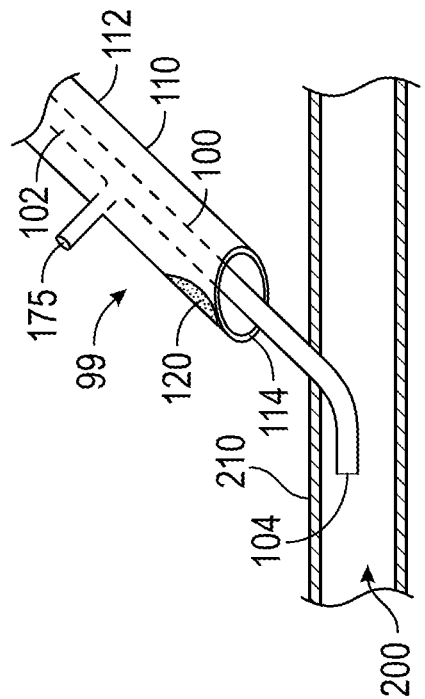
FIGS. 4A-4H show a non-limiting example of a method for opening and closing a hole in a vessel of the present invention.
Figure 4B:
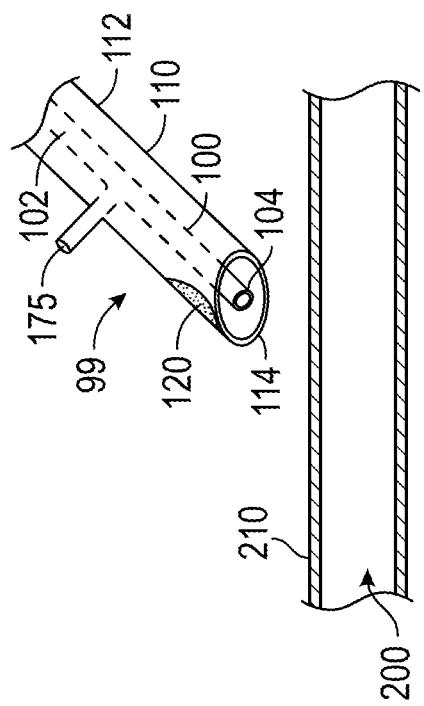
Figure 4C:
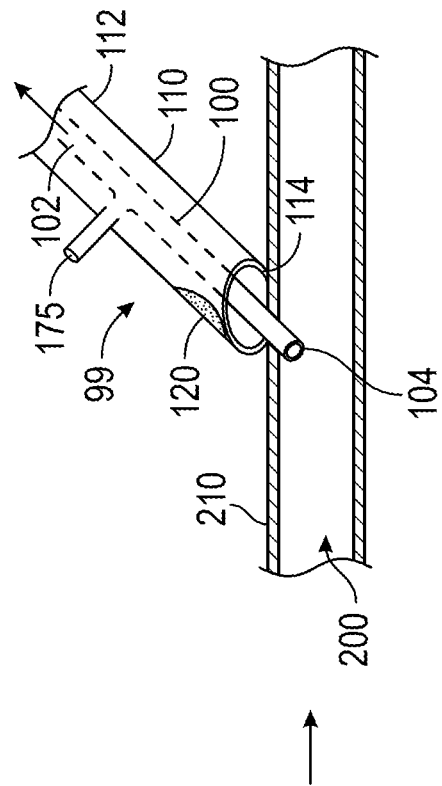
Figure 4D:
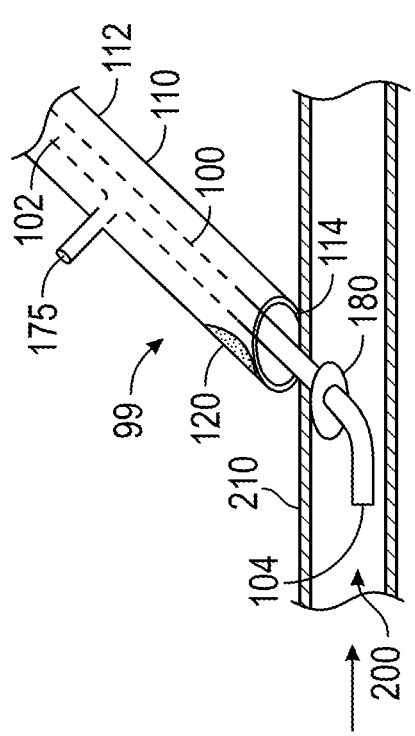
Figure 4E:
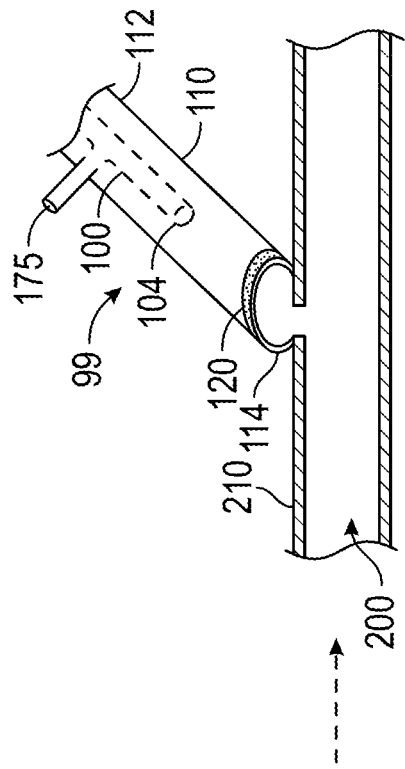
Figure 4G:
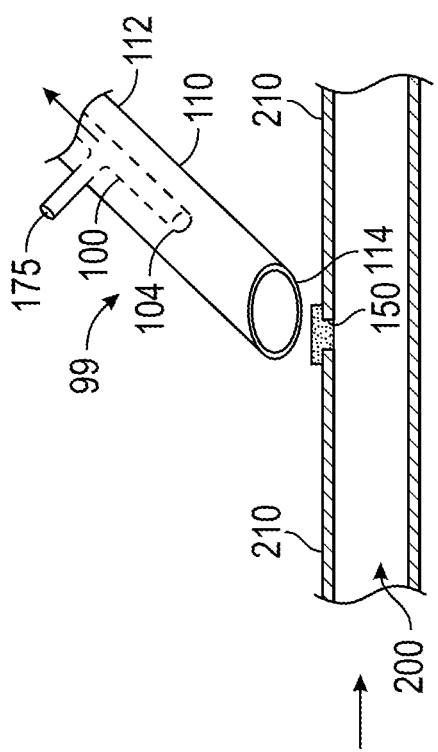
Figure 4F:
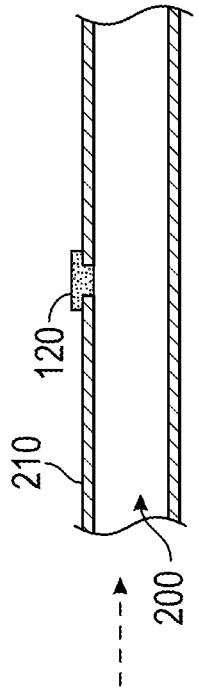
Figure 4H:
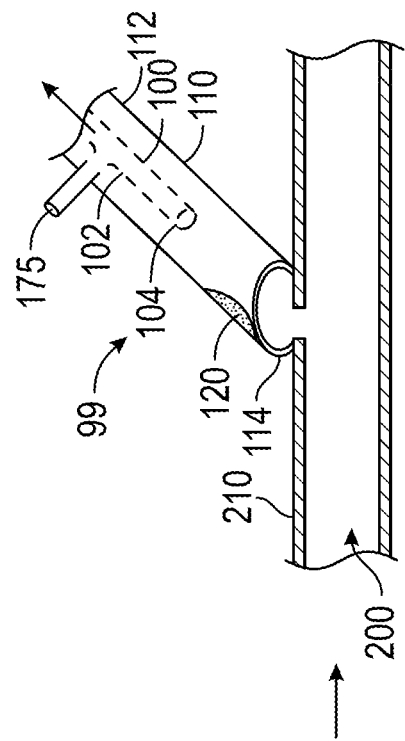
Figure 5A:
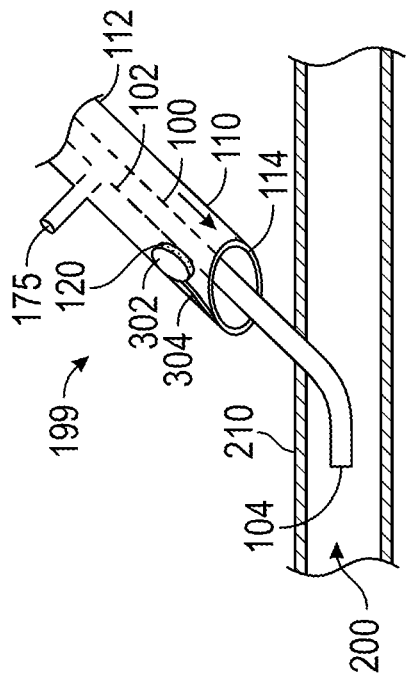
FIGS. 5A-5H show a non-limiting example of a method for opening and closing a hole in a vessel of the present invention using a flexible hinge to aid in closure.
Figure 5C:
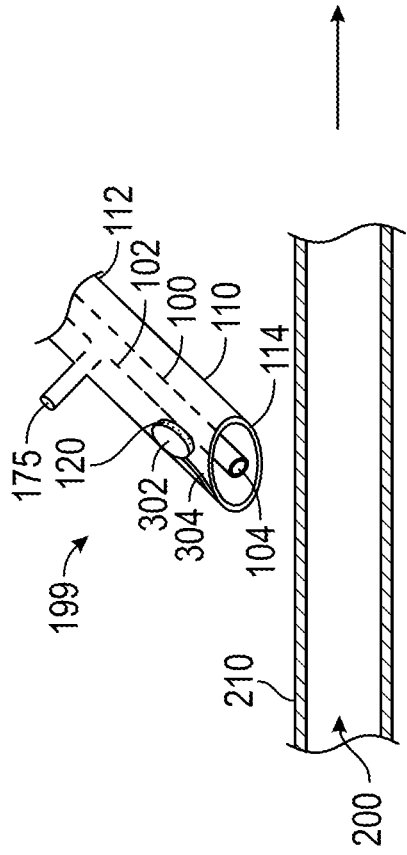
Figure 5B:
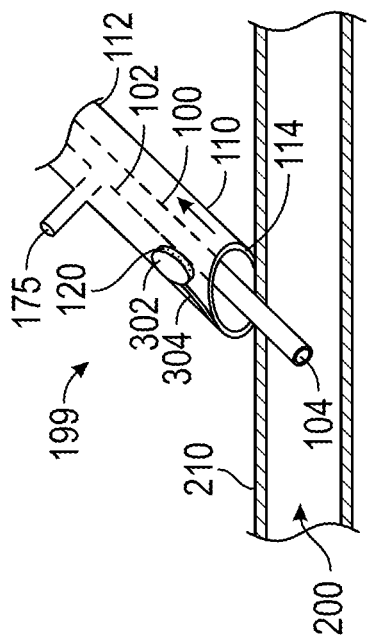
Figure 5D:
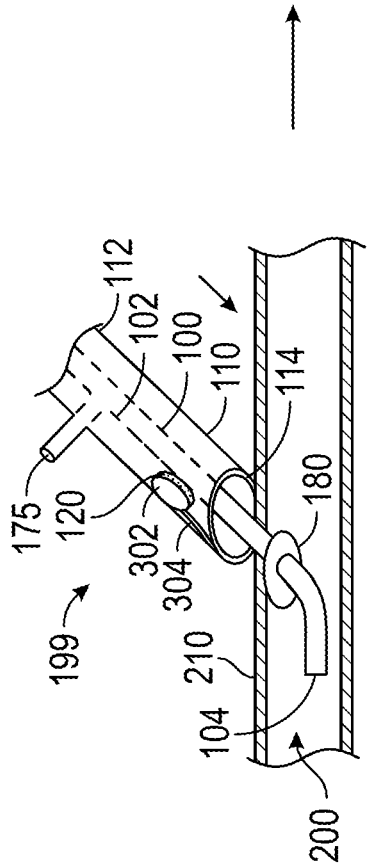
Figure 5E:
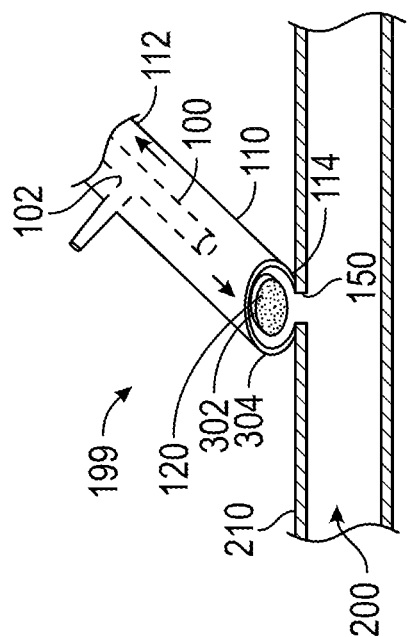
Figure 5G:
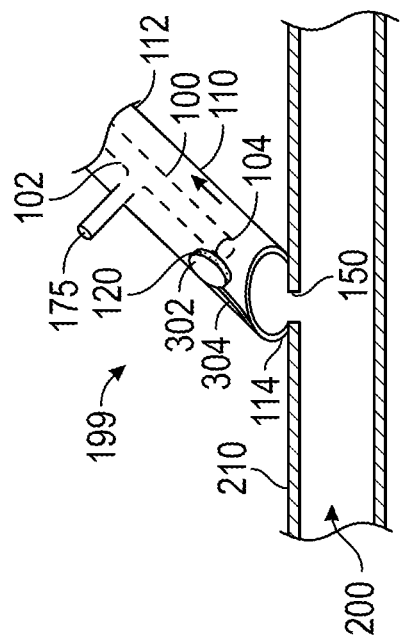
Figure 5F:
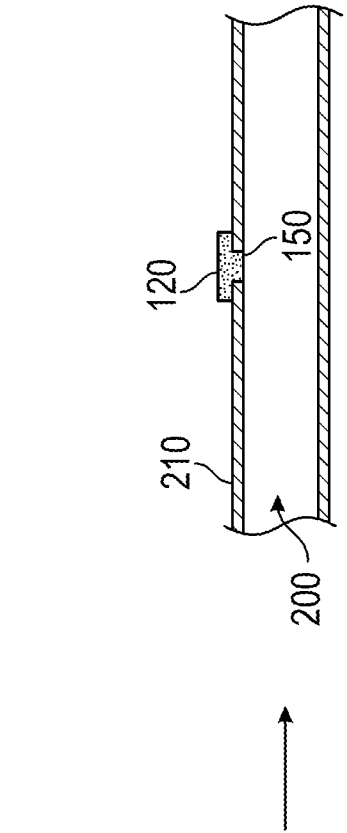
Figure 5H:
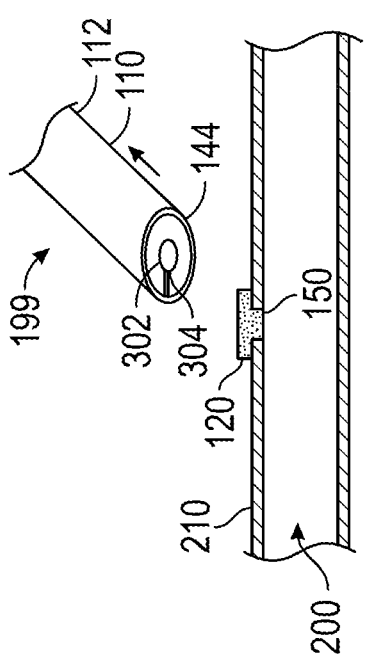
Figure 6A:
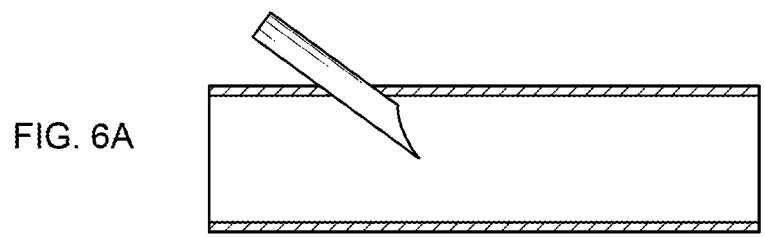
FIGS. 6A-6F show a non-limiting example of a method for opening a hole in a vessel using a needle, a wire, and a dilator in conjunction with a tube.
Figure 6B:
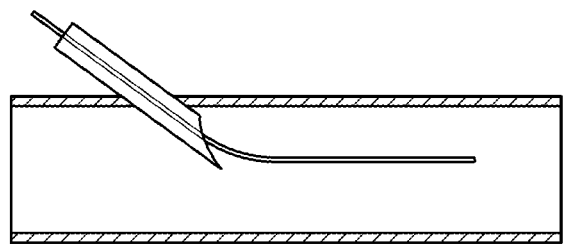
Figure 6C:
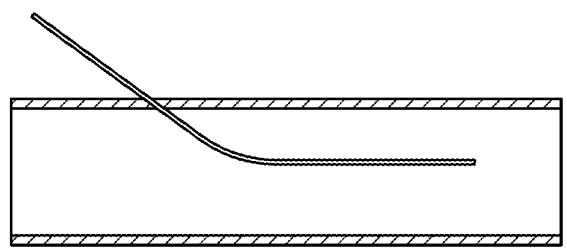
Figure 6D:
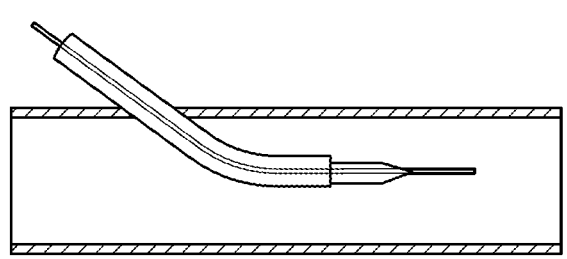
Figure 6E:
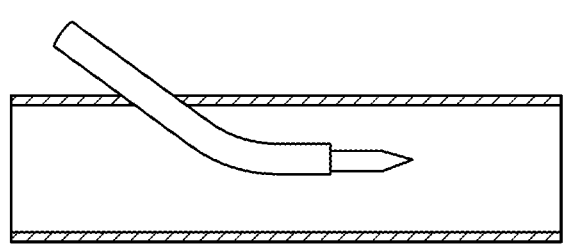
Figure 6F:
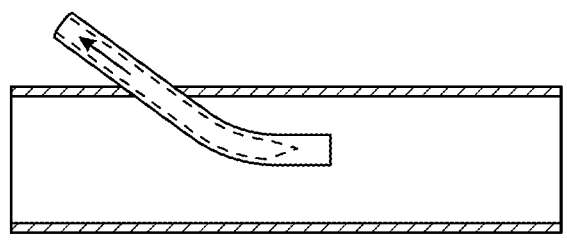
Figure 7A:
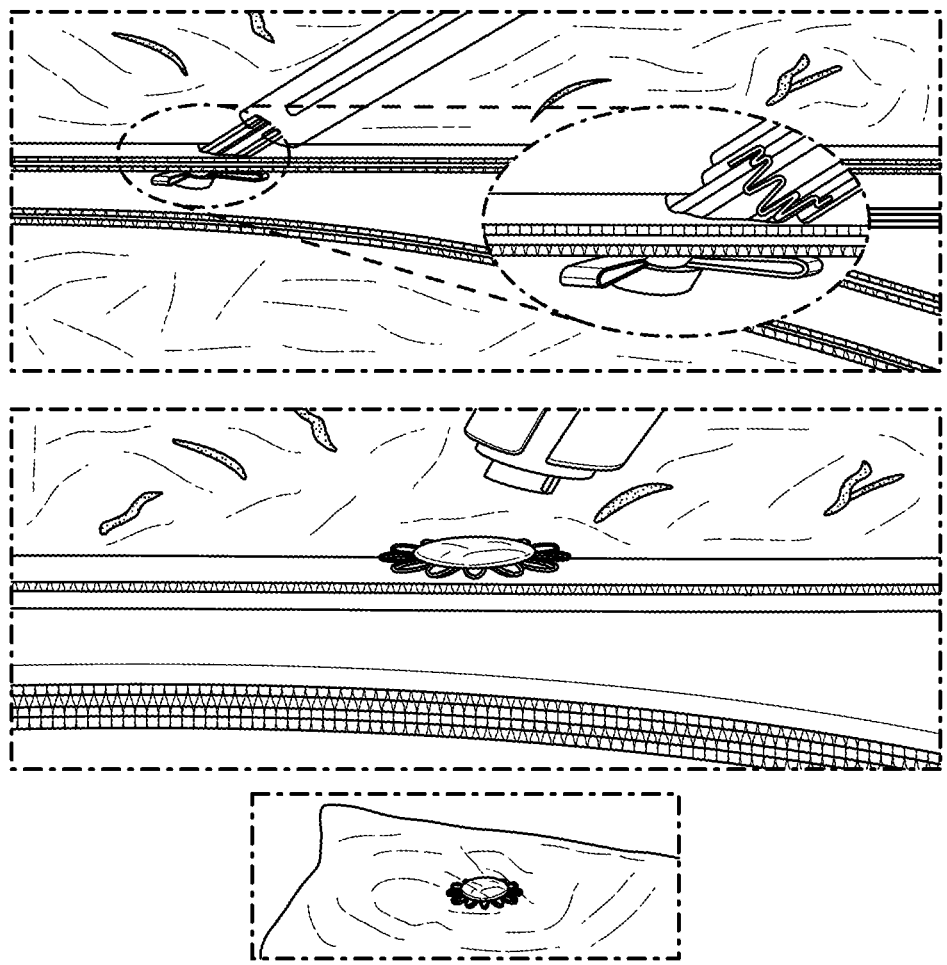
FIG. 7A shows a suture-mediated closure system that cinches the arterial opening with a suture (e.g., Perclose Proglide®, Starclose®).
Figure 7B:
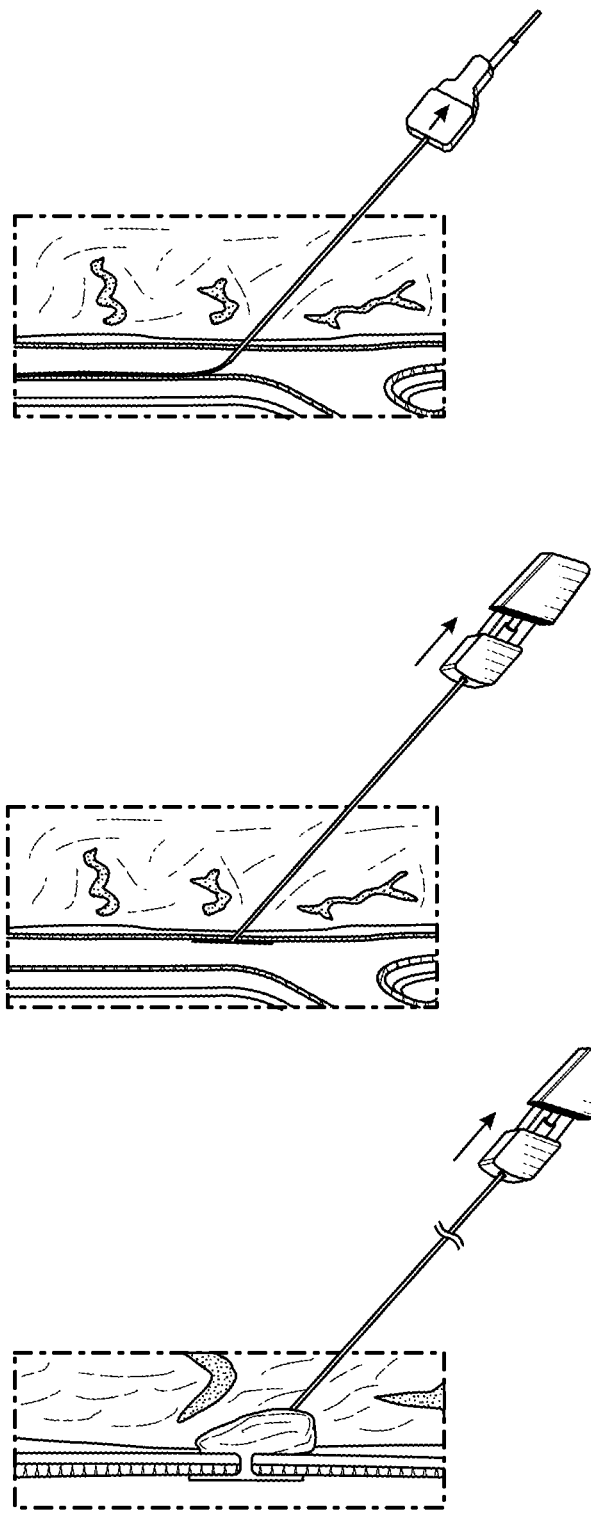
FIG. 7B shows the prior art, Angio-Seal™, which leaves a footplate inside the artery up against the arterial opening and risks clotting in artery or narrowing the artery.

In some embodiments, the present invention features a closure mechanism (120) attached to a flexible hinge (300) to aid in the application of said closure mechanism (120) to a hole (150) in a vessel (200). The flexible hinge (300) may be positioned between an outer tube (110) and an inner tube (100) and may comprise a closure holder (302) and an arm (304), the arm (304) having a distal end (312) and a proximal end (314). The closure holder (302) may be disposed at the distal end (312) of the arm (304) and the proximal end (314) of the arm (304) may be pivotally attached to an inner surface of a distal end (114) of the outer tube (110). The closure mechanism (120) may be disposed at the closure holder (302). The flexible hinge (300) may be positioned such that the inner tube (100) when extended holds the flexible hinge (300) in a tension state. In some embodiments, the flexible hinge (300) is a memory wire. When the inner tube (100) moves to a non-extended state, the inner tube (100) no longer holds the flexible hinge (300) in a tension state, causing the flexible hinge (300) to move to a memory state. The movement from the tension state to the memory state may cause the closure mechanism (120) to be moved to a released position (122) as the closure mechanism (120) detaches from the closure holder (302). The detached closure mechanism (120) may now be in an enclosed state (124). Retracting the outer tube (110) may cause the closure mechanism (120) to remain in an engaged position (126). In some embodiments, the system of the present invention may comprise more than one flexible hinge (300), each flexible hinge (300) closure holder (302) having a closure mechanism (120) or a portion of a closure mechanism (120) disposed upon it. Such embodiments may comprise a first flexible hinge and a second flexible hinge, wherein the first flexible hinge may have a first closure holder (302) that is smaller than a second closure holder (303) and a first closure mechanism (120) that is smaller than a second closure mechanism (121). The first flexible hinge may have a first arm (304) that is shorter than a second arm (305) of the second flexible hinge, such that the first flexible hinge will move to the memory state first and the second flexible hinge will move to the memory state second and detach the second closure mechanism (121) on top of the first closure mechanism (120), as seen in FIG. 3B.

Non-limiting examples of a closure mechanism (120) comprise a metal clip, a hemostatic foam, a suture, a biodegradable patch, an adhesive gel, and/or other substances that effectively cover, seal, and/or close the hole (150) in the vessel (200) in a fail-safe manner that prevents re-opening of the hole (150). In one embodiment, the detachable closure device (120) is juxtaposed along the distal end of the outer tube (114) and is exposed when the inner tube (100) is separated from the outer tube (110). Once the closure device (120) is exposed and is in a release position (122), the closure device (120) moves to cover the vessel hole (150) and attaches onto the outside of the blood vessel (210) in an enclosed position (124). The closure device (120) is then detached from the outer tube (110) by a mechanical release, electrolytic, thermal, or chemical disconnection of the attachment at the detachment zone (130) and the outer tube (110) is removed leaving the closure device (120) in an engaged position (126) to close the arterial opening (150). Therefore, the present invention features a single system that integrates the mechanisms that open a blood vessel (200) as well as closes the opening to the blood vessel (200).

In some embodiments, the all-in-one opening/access and closing device (99) of the present invention may comprise a first flexible hinge (300) comprising a closure holder (302) having a closure mechanism (120) disposed at a first side, an arm (304) having a distal end (312) and a proximal end (314), and a plunger (1302). The closure holder (302) may be disposed at the distal end (312) of the arm (304) and the plunger (1302) may be disposed through the closure holder (302) and exposed at a second side of the closure holder (302) such that applying force to the second side of the closure holder (120) pushes the plunger (1302) through the closure holder (302) and dislodges the closure mechanism (120) from the closure holder (120). The flexible hinge (300) may be attached to a distal end of an outer tube (114) by the proximal end (314). The device (99) may further comprise a second flexible hinge comprising a hammer (1312) and an arm (305) having a second distal end (313) and a second proximal end (315). The hammer (1312) may be disposed at the second distal end (313) and the second flexible hinge may be attached to the distal end of the outer tube (114) by the second proximal end (315). The arm of the first flexible hinge (304) may be shorter than the arm of the second flexible hinge (305) such that, as an inner tube (100) retracts, the first flexible hinge (304) moves from a tension state to a memory state before the second flexible hinge does so. The first flexible hinge (300) moving from the tension state to the memory state may cause the closure mechanism (120) to cover a hole (150) in a vessel (200) created by the inner tube (100). The second flexible hinge moving from the tension state to the memory state may cause the hammer (1312) to apply force to the plunger (1302) and cause the plunger (1302) to dislodge the closure mechanism (120) and attach the closure mechanism (120) to an outer surface of the vessel (210). The all-in-one opening and closure mechanism (99) may then be retracted, leaving the closure mechanism (120) in an enclosed state (126). In summary, the first flexible hinge (300) positions the closure mechanism (120) over the hole (150) in the vessel (200) and the second flexible hinge knocks the closure mechanism (120) into place.

In some embodiments, the all-in-one opening and closure device (99) of the present invention may comprise a flexible hinge (300) comprising a closure holder (302) having a closure mechanism (120) disposed at a first side, and an arm (304) having a distal end (312) and a proximal end (314). The closure holder (302) may be disposed at the distal end (312) and the flexible hinge (300) may be attached to a distal end of an outer tube (114) by the proximal end (314). The first flexible hinge (300) moving from a tension state to a memory state may cause the closure mechanism (120) to cover a hole (150) in a vessel (200) created by an inner tube (100). In some embodiments, the closure holder (302) may comprise a dissolvable material and a dissolving chemical (1330) may be directed through the all-in-one opening and closure device (99) such that the closure holder (302) dissolves and leaves the closure mechanism (120) attached to the outer surface of the vessel (210). The device (99) may be removed from the vessel (200), leaving the closure mechanism (120) in an enclosed state (126). The dissolving chemical (1330) may comprise a chemical or a combination of a plurality of chemicals known to one skilled in the art.

Other forms of detaching the closure mechanism (120) from the flexible hinge (300) may be forms of thermal/electrical detachment mechanisms (a heated/electrically charged wire directed through the all-in-one opening/access and closure device (199) to melt the closure holder (302) and attach the closure mechanism (120) to the vessel (200)). Additional detachment mechanisms may be mechanisms similar to those outlined in *J Neurointervent Surg* 2013; Issue 5: Pages 104-109, the specification of which is incorporated herein in its entirety by reference.

The present invention also features a method for forming and closing a hole (150) in a blood vessel (200), e.g., an artery or a vein. The method comprises providing the all-in-one system (99) that forms and rapidly closes vascular holes. In brief, the system comprises an inner tube (100) with a first proximal end (102) and a first distal end (104), an outer tube (110) that is concentric to and/or surrounds the first tube (100) comprising a second proximal end (112) and a second distal end (114), and a closure mechanism (120) effectuated by the outer tube (110). The distal end of the inner tube (102) is disposed onto the outer surface of a vessel (210) and inserted through the vessel (200), thereby forming a hole (150) in the surface of the vessel (210), and allowing the distal end (114) of the second tube (110) disposing the closure mechanism (120) to be at or near the vessel hole (150). The distal end of the inner tube (104) is then separated or withdrawn from the vessel (200) releasing the closure mechanism (120) onto the surface of the vessel (210) at or near the vessel hole (150), effectively covering the vessel hole (150). The closure device (120) then detaches from the distal end of the outer tube (114) by a mechanical release, electrolytic or thermal disconnection of the attachment at the detachment zone (130) and removing the outer tube (110) leaves the closure device (120) to effectively close the vessel hole (150).

In some embodiments, the closure mechanism (120) is selected from a group consisting of a metal clip, a hemostatic foam, a suture, a biodegradable patch, and an adhesive gel. The closure mechanism (120) is a device or a substance that effectively covers, seals, or closes the hole (150) in the vessel (200) in a fail-safe manner that prevents re-opening of the hole (150).

In some embodiments, the method for closing a vessel hole (150) comprises first withdrawing the inner tube (100) by twisting the proximal end of the inner tube (102) to release the closure device (120). For example, the proximal end of the inner tube (102) may be threaded (as shown in FIG. 2A) so that twisting it can withdraw the inner tube (100), detaching and releasing the closure device (120). Once the closure device (120) is in a released position (122), the closure device (120) releases to cover the vessel hole (150) and attaches onto the surface of the vessel (210) to be in an enclosed position (124). After detaching the closure device (120) from the distal end of the outer tube (114), the outer tube (110) is removed leaving the closure device (120) in an engaged position (126) to effectively close the vessel hole (150). In some embodiments, the method further features prior to closing the hole (150), a medical device is inserted through the hole (150) via the inner tube (100) and into the vessel (200), wherein the medical device is selected from a group consisting of a catheter, stent, balloon, therapeutic drug infusions, and wire. In preferred embodiments, the features a second tube (110) that is shorter than the first tube (100).

Referring now to FIG. 1, the present invention features an all-in-one blood vessel entry and closure system (99). The system comprises: a first tube (100), a second tube (110), and a closure mechanism (120). The first tube (100) comprises a first inner surface (106), a first outer surface (108), a first proximal end (102), and a first distal end (104). The first distal end (104) is inserted through the skin to create an opening (150) in a vessel (200) that provides percutaneous access and entry to the vessel (200). The second tube (110) is concentric to and/or surrounds the first tube (100). The second tube (110) comprises a second inner surface (116), a second outer surface (118), a second proximal end (112), and a second distal end (114). The second distal end (114) is inserted through the skin to provide the same percutaneous access location to the vessel as the first tube (100) and allowing the closure mechanism (120) to be at or near the vessel hole (150). The closure mechanism (120) effectuated in a space (125) between the second inner surface (116) and the first outer surface (108), wherein the closure mechanism (120) closes the opening (150) to the vessel (200).

Referring now to FIG. 2A, the present invention features an inner tube (100), including the use of a balloon access port (175). The balloon access port may fluidly connect to a balloon (180) in a deflated state through a balloon inflation tube (176). The balloon inflation tube (176) may fluidly connect to the balloon (180) through a balloon inflation orifice (177). The balloon inflation port (175) may be used to direct air through the balloon inflation tube (176) to bring the balloon (180) to an inflated state to locate a hole in the vessel (150), as seen in FIG. 2B. The inner tube (100) comprises a first inner surface (106), a first outer surface (108), a first proximal end (102), and a first distal end (104). As seen in FIG. 2C, the first distal end (104) is disposed on the surface of the vessel (210), creates an opening or a hole (150) in a vessel (200) that provides access and entry to the vessel (200), and enters the vessel (200) to serve as a sheath. The present invention may further comprise an outer tube (110) that is concentric to and/or surrounds the first tube (100). The outer tube (110) comprises a second inner surface (116), a second outer surface (118), a second proximal end (112), and a second distal end (114). The second distal end (114) is also disposed on the outer surface of the vessel (210) without entering the vessel (200) and affords the same access location to the vessel (200) as the first tube (100) allowing the closure mechanism (120), which is disposed along the distal end of the outer tube (114), to be at or near the vessel hole (120).

The closure mechanism (120) can then close the opening (150) to the vessel (200). For example, when the inner tube (100) is separated from the outer tube (110) to expose the closure device (120), the closure device (120) is in a release position (122) to cover the vessel hole (150) and attach onto the outside of the vessel (210) in an enclosed position (124). The closure device (120) is then detached from the outer tube (110) and the outer tube (110) is removed leaving the closure device (120) in an engaged position (126) to effectively close the vessel hole (150).

In some embodiments, the first distal end of the first tube (104) and the distal end of the second tube (114) are inserted through the skin for percutaneous access to the vessel (200). In other embodiments, the distal end of the first tube (104) and the distal end of the second tube (114) can directly contact an organ (e.g., stomach, colon, etc). For example, the system (99) could replace standard laparoscopic tubes and be used in surgery to create holes within the abdomen.

Referring now to FIGS. 4A-4H, the present invention features a method for forming and closing a hole (150) in a vessel (200). The method comprises providing (step a) an all-in-one device (99) that comprises an inner tube (100), an outer tube (110), and a closure mechanism (120). The inner tube (100) comprises a first proximal end (102) and a first distal end (104). The second tube (110) is concentric to and/or surrounds the first tube (100) and comprises a second proximal end (112) and a second distal end (114). The closure mechanism (120) can be a device or substance (120) juxtaposed along the distal end of the outer tube (114). The distal end of the inner tube (104) is then disposed onto the surface of the vessel (200) and inserted through the surface of the vessel (210) as seen in FIGS. 6A-6F, thereby forming a hole (150) through the surface of the vessel (200). An inflatable balloon (180) disposed on the inner tube (100) may be inflated through a balloon inflation tube (176) disposed within a balloon inflation port (175) in order to localize the hole (150) from the inside. Before retracting the inner tube (100) from the vessel (200), the inflatable balloon (180) is deflated. The distal end of the inner tube (104) is then withdrawn from the vessel (200) releasing the closure device or substance (120) onto the surface of the vessel (210) and detaching the closure device (120) from the distal end of the outer tube (114). The outer tube (110) is then removed, leaving the closure device (120) to effectively close the vessel hole (150).

Referring now to FIGS. 5A-5H, the present invention features a method for forming and closing a hole (150) in a vessel (200). The method comprises providing an all-in-one device (199) that comprises an inner tube (100), an outer tube (110), and a closure mechanism (120) disposed on a closure holder (302) of a flexible hinge (300), the flexible hinge (300) being positioned between the outer tube (110) and the inner tube (100). FIGS. 3A-3B shows non-limiting examples for the structure and placement of the flexible hinge (300). The flexible hinge (300) may comprise a closure holder (302) and an arm (304), the arm (304) having a distal end (312) and a proximal end (314). The closure holder (302) may be disposed at the flexible hinge distal end (312) and the arm (304) may be pivotally attached to the outer tube (110) in a space (125) between the outer tube (110) and the inner tube (100), near the outer tube distal end (114). The flexible hinge (300) may begin in a tension state. In some embodiments, the flexible hinge (300) is a memory wire. The inner tube (100) comprises a first proximal end (102) and a first distal end (104). The second tube (110) is concentric to and/or surrounds the first tube (100) and comprises a second proximal end (112) and a second distal end (114). The distal end of the inner tube (104) is then disposed onto the surface of the vessel (210) and inserted through the surface of the vessel (210) as seen in FIGS. 6A-6H, thereby forming a hole (150) through the surface of the vessel (210). A balloon (180) is inflated within the vessel (200) through a balloon inflation tube (176) disposed within a lumen (175) to aid in finding the point of entry. The balloon (180) is then deflated and the distal end of the inner tube (104) is then withdrawn from the vessel (200) causing the flexible hinge (300) to be moved into a memory position with enough force to release the closure device or substance (120) onto the surface of the vessel (210) and detach the closure device (120) from the closure holder (120). The outer tube (110) is then removed, leaving the closure device (120) to effectively close the vessel hole (150).

Referring now to FIGS. 6A-6H, the present invention utilizes a method for opening a hole (150) in a vessel (200) to allow entry for a tube (100). A needle may first be inserted through an outer surface of the vessel (210) and a wire may be directed through the needle. The wire allows for entry into the vessel (200) to be maintained after the removal of the needle. The needle is then removed and a section of the wire outside of the vessel (200) is strung through an entry mechanism. The entry mechanism may comprise a tube (100) having a distal end (104) and a proximal end (102), and a dilator directed through the tube (100). The dilator may comprise a blunt tapered tip that protrudes from the distal end of the tube (104), and the dilator may be removable from the entry mechanism by a handle protruding from the proximal end of the tube (102). The entry mechanism may use the wire as a guide and the blunt tapered tip of the dilator may allow the entry mechanism to pass through the outer surface of the vessel (210). The wire may then be removed from the vessel (200), and the dilator may then be pulled out of the entry mechanism by the handle, leaving the tube (100) inside the vessel (200) for further action.

In some embodiments, the all-in-one access and closure device (99) of the present invention may be 2-8 mm in diameter and 5-20 cm in length. An inner tube (100) of the present invention may be 1-4 mm in diameter and 4-15 cm in length. The inner tube (100) may be of a size capable of entering a vessel (200) and/or of a size capable of containing a catheter. An outer tube (110) of the present invention may be 2-6 mm in diameter and 1-3 cm in length. The outer tube (110) may be larger in size than the inner tube (100) and may be greater in size to a diameter of the inner tube (100). The closure mechanism (120) may be lesser in size to a diameter of the outer tube (110).

Example

The following are non-limiting examples of the present invention. It is to be understood that said examples are not intended to limit the present invention in any way. Equivalents or substitutes are within the scope of the present invention.

The following example describes emergency treatment strategies for an active stroke involving an all-in-one vessel opening and closure device (99).

A 80-year-old male shows signs of a stroke (numbness in one side of his face, paralysis of arm and leg on one side, confusion, etc), prompting his wife to call an ambulance. Paramedics arrive on the scene and quickly confirm that the man is indeed having a stroke and he is taken to a comprehensive stroke center where the imaging studies confirm he has a clot in his carotid artery intracranially preventing blood flow to the brain. The stroke surgeon determines that removal of the clot endovascularly is the best course of action. The surgeon uses the all-in-one vessel opening and closure device (99) to create an opening (150) in the carotid artery, granting intra-arteral access through an inner tube (100) as an outer tube (110) rests on an outer surface of the carotid artery surrounding the inner tube (100). A balloon (180) disposed on the inner tube (100) is inflated to allow temporary flow arrest while the intra-arterial access granted by the inner tube (100) also functions as an aspiration catheter to remove the clot and restore blood flow to the brain. Upon removing the clot, the inner tube (100) is retracted from the carotid artery. As the inner tube (100) retracts, a closure mechanism (120) disposed between the inner tube (100) and the outer tube (110) immediately activates, sealing the hole (150) and preventing bleeding. The man is taken to the intensive care unit to monitor his status and to aid in his recovery. No side effects are reported from using the all-in-one vessel opening and closure device (99).

The following example describes strategies for interventional cardiology utilizing an all-in-one vessel opening and closure device (99).

A 75-year-old female patient meets with a cardiologist and reports that she is experiencing shortness of breath, chest pain, and fatigue. After performing tests, her cardiologist diagnoses her with aortic valve stenosis and recommends that a transcatheter aortic valve replacement (TAVR) procedure is the best course of action. Her anatomy prevents safe entry from the traditional femoral artery route. During surgery, the patient is put under anesthesia and the all-in-one vessel opening and closure device (99) is used to create an opening (150) in the carotid artery, granting intra-arterial access through an inner tube (100) as an outer tube (110) rests on an outer surface of the carotid artery surrounding the inner tube (100). A catheter with a biological tissue valve disposed on it is directed through the inner tube (100), through the carotid artery, and to the aortic valve. The biological tissue valve is applied within the aortic valve to restore proper blood flow. After applying the new valve, the catheter and inner tube (100) are retracted from the carotid artery. As the inner tube (100) retracts, a closure mechanism (120) disposed between the inner tube (100) and the outer tube (110) immediately activates, sealing the hole (150) and preventing bleeding. The patient is hospitalized for a week to recover and to monitor for any changes in her condition.

Five weeks later, she meets with her cardiologist for a follow-up and reports that her symptoms have gone away. Her cardiologist determines that the TAVR procedure is successful and the patient is fully recovered. No side effects are reported from using the all-in-one vessel opening and closure device (99).

In another example, a 75-year-old female patient meets with a cardiologist and reports the same symptoms as the previous case. After performing tests, her cardiologist diagnoses her with aortic valve stenosis and recommends that a TAVR procedure is the best course of action. Her anatomy DOES allow for safe entry to the heart through the traditional femoral artery route. During surgery, the patient is put under anesthesia and the all-in-one vessel opening and closure device (99) is used to create an opening (150) in the femoral artery, granting intra-arterial access through an inner tube (100) as an outer tube (110) rests on an outer surface of the femoral artery surrounding the inner tube (100). A catheter with a biological tissue valve disposed on it is directed through the inner tube (100), through the femoral artery, and to the aortic valve. The biological tissue valve is applied within the aortic valve to restore proper blood flow. After applying the new valve, the catheter and inner tube (100) are retracted from the femoral artery. As the inner tube (100) retracts, a closure mechanism (120) disposed between the inner tube (100) and the outer tube (110) immediately activates, sealing the hole (150) and preventing bleeding. The patient is hospitalized for a week to recover and to monitor for any changes in her condition. Five weeks later, she meets with her cardiologist for a follow-up and reports that her symptoms have gone away. Her cardiologist determines that the TAVR procedure is successful and the patient is fully recovered. No side effects are reported from using the all-in-one vessel opening and closure device (99).

The following items are non-limiting embodiments of the present invention:

1. An all-in-one system (99) for forming and closing a hole (150) in a vessel (200), the system comprising:
    a) a first tube (100) that forms the hole (150) in the vessel (200), wherein the first tube (100) enters the vessel (200);
    b) a second tube (110) that surrounds the first tube (100); wherein the second tube (110) surrounds the first tube (100) and does not enter the vessel (200); and
    c) a closure mechanism (120), wherein the closure mechanism (120) is disposed in a space (125) between the second tube (110) and the first tube (100), wherein the closure mechanism (120) closes the opening (150) in the vessel (200).
2. The system of item 1, wherein the vessel (200) is a vein or an artery.
3. The system of item 1, wherein the closure mechanism (120) is a closing device or a substance that effectively covers, seals, or doses the hole (150) in the vessel (200) in a fail-safe manner that prevents re-opening of the hole (150).
4. The system of item 3, wherein the closure mechanism (120) is selected from a group consisting of a metal clip, a hemostatic foam, a suture, a biodegradable patch, and an adhesive gel.
5. The system of item 1 further comprising a balloon inflation port (175) integrated with the first tube (100).
6. The system of item 5, wherein the first tube (100) comprises a first lumen and a second lumen, wherein the first lumen is configured to have a medical device inserted therein, and wherein the second lumen is fluidly coupled to the balloon inflation port (175).
7. The system of item 6 further comprising an inflatable balloon (180) located at or near a distal end (104) of the first tube (100) and fluidly coupled to the balloon inflation port (175) via the second lumen, wherein the balloon (180) is configured to be inflated locating the hole (150) in the vessel (200).
8. The system of item 6, wherein the medical device is a catheter, stent, balloon, therapeutic drug infusion, or wire.
9. The system of item 1, wherein a distal end of the first tube (104) is radiodense for visibility under fluoroscopy or echogenic for visibility with ultrasound.
10. The system of item 1, wherein a distal end of the second tube (114) is radiodense for visibility under fluoroscopy or echogenic for visibility with ultrasound.
11. The system of item 1, wherein the first tube (100) further comprises a pressure monitoring sensor, a flow monitoring sensor, or both.
12. The system of item 1, wherein the second tube (110) is equipped with a pressure monitoring sensor, a flow monitoring sensor, or both.
13. The system of item 1, wherein the second tube (110) is configured as to not enter into or puncture the vessel (200).
14. The system of item 13, wherein the second tube (110) is configured to have a larger diameter than the first tube (100), to be shorter than the first tube (100), and/or to have a blunt distal end (104).
15. A percutaneous blood vessel opening and closure all-in-one system (99) comprising:
    a) a first tube (100) comprising a first inner surface (106), a first outer surface (108), a first proximal end (102), and a first distal end (104), wherein the first distal end (104) is inserted through the skin, disposed on the surface of the blood vessel (200), and creates an opening or hole (150) in the vessel (200) and enters the vessel (200) providing percutaneous access and entry to the vessel (200);
    b) a second tube (110) that surrounds the first tube (100), wherein the second tube (110) comprises a second inner surface (116), a second outer surface (118), a second proximal end (112), and a second distal end (114), wherein the second distal end (114) has a tip (119) that is inserted through the skin to provide the same percutaneous access location to the vessel surface (210) as the first tube (100) and does not enter the vessel (200); and
    c) a closure mechanism (120) effectuated in a space (125) between the second inner surface (116) and the first outer surface (108), wherein the closure mechanism (120) is at or near the vessel opening or hole (150) to effectively dose the opening or hole (150) to the vessel (200);
    wherein the system (99) integrates the opening (150) of the vessel (200) as well as closing the vessel opening (150).
16. The system of item 15, wherein the vessel (200) is an artery or vein.
17. The system of item 15, wherein the closure mechanism (120) is selected from a group consisting of a metal clip, a hemostatic foam, a suture, a biodegradable patch, and an adhesive gel, wherein the closure mechanism (120) effectively covers, seals, or closes the hole (150) in the vessel (200) in a fail-safe manner that prevents re-opening of the hole (150).

18. The system of item 15 further comprising a balloon inflation port (175) integrated with the first tube (100).
19. The system of item 18, wherein the first tube (100) comprises a first lumen and a second lumen, wherein the first lumen is configured to have a medical device inserted therein, and wherein the second lumen is fluidly coupled to the balloon inflation port (175).
20. The system of item 19 further comprising an inflatable balloon (180) located at or near a distal end of the first tube (104) and fluidly coupled to the balloon inflation port (175) via the second lumen, wherein the balloon (180) is configured to be inflated locating the hole (150) in the vessel (200).
21. The system of item 19, wherein the medical device is a catheter, stent, balloon, therapeutic drug infusion, or wire.
22. The system of item 15, wherein a distal end of the first tube (104) is radiodense for visibility under fluoroscopy or echogenic for visibility with ultrasound.
23. The system of item 15, wherein a distal end of the second tube (114) is radiodense for visibility under fluoroscopy or echogenic for visibility with ultrasound.
24. The system of item 15, wherein the first tube (100) further comprises a pressure monitoring sensor, a flow monitoring sensor, or both.
25. The system of item 15, wherein the second tube (110) is equipped with a pressure monitoring sensor, a flow monitoring sensor, or both.
26. The system of item 15, wherein the second tube (110) is configured as to not enter into or puncture the vessel (200).
27. The system of item 26, wherein the second tube (110) is configured to have a larger diameter than the first tube (100), to be shorter than the first tube (100), and/or to have a blunt distal end (114).
28. A percutaneous blood vessel opening and closure system (99) comprising:
    a) an inner tube (100) comprising a proximal end (102) and a distal end (104), wherein the distal end (104) in inserted through the skin, disposed on the surface of the vessel (200), and creates an opening or hole (150) in a vessel (200) and enters the vessel (200) to provide percutaneous access and entry to the vessel (200);
    b) an outer tube (110) that surrounds the inner tube (100), wherein the outer tube (110) is positioned relative to the inner tube (100) so that the distal end of the outer tube (114) is disposed at or near the vessel opening or hole (150) and does not enter the vessel (200); and
    c) a detachable closure device (120) juxtaposed along the distal end (114) of the outer tube (110),
    wherein the inner tube (100) is separable from the outer tube (110) to expose the closure device (120), wherein the closure device (120) is in a release position (122) to cover the vessel hole (150) and attach onto the outside of the vessel (210) in an enclosed position (124), wherein the closure device (120) is then detached from the outer tube (110) and the outer tube (110) is removed leaving the closure device in an engaged position (126) to close the vessel opening (150),
    wherein the system (99) integrates the opening of the vessel (200) as well as closing the vessel opening (150).
29. The system of item 28, wherein the vessel (200) is an artery or a vein.
30. The system of item 28, wherein the closure device (120) is attached to the outer tube (110) via a removable attachment disposed at a detachment zone (130), wherein the detachment zone (130) is located at or near the distal end of the outer tube (114).
31. The system of item 28, wherein the closure device (120) is detached from the outer tube (110) by a mechanical release, or electrolytic or thermal disconnection.
32. The system of item 28, wherein the closure device (120) comprises a metal clip, a hemostatic foam, a suture, a biodegradable patch, an adhesive gel, and/or a device or a substance that effectively covers, seals, or closes the hole (150) in the vessel (200) in a fail-safe manner that prevents re-opening of the vessel hole (150).
33. The system of item 28 further comprising a balloon inflation port (175) integrated with the inner tube (100).
34. The system of item 33, wherein the inner tube (100) comprises a first lumen and a second lumen, wherein the first lumen is configured to have a medical device inserted therein, and wherein the second lumen is fluidly coupled to the balloon inflation port (175).
35. The system of item 34 further comprising an inflatable balloon (180) located at or near a distal end (104) of the inner tube (100) and fluidly coupled to the balloon inflation port (175) via the second lumen, wherein the balloon is configured to be inflated locating the hole (150) in the vessel (200).
36. The system of item 34, wherein the medical device is a catheter, stent, balloon, therapeutic drug infusion, or wire.
37. The system of item 28, wherein a distal end of the inner tube (104) is radiodense for visibility under fluoroscopy or echogenic for visibility with ultrasound.
38. The system of item 28, wherein a distal end of the outer tube (114) is radiodense for visibility under fluoroscopy or echogenic for visibility with ultrasound.
39. The system of item 28, wherein the inner tube (100) further comprises a pressure monitoring sensor, a flow monitoring sensor, or both.
40. The system of item 28, wherein the outer tube (110) is equipped with a pressure monitoring sensor, a flow monitoring sensor, or both.
41. The system of item 28, wherein the outer tube (110) is configured so as to not enter into or puncture the vessel (200).
42. The system of item 41, wherein the outer tube (110) is configured to have a larger diameter than the inner tube (100), to be shorter than the inner tube (100), and/or has a blunt distal end (114).
43. A percutaneous blood vessel opening and closure system (199) comprising:
    d) an inner tube (100) comprising a proximal end (102) and a distal end (104), wherein the distal end (104) in inserted through the skin, disposed on the surface of the vessel (200), and creates an opening or hole (150) in a vessel (200) and enters the vessel (200) to provide percutaneous access and entry to the vessel (200);
    e) an outer tube (110) that surrounds the inner tube (100), wherein the outer tube (110) is positioned relative to the inner tube (100) so that the distal end of the outer tube (114) is disposed at or near the vessel opening or hole (150) and does not enter the vessel (200);

f) a flexible hinge (300) having a closure holder (302) and an arm (304), the arm having a distal end (312) and a proximal end (314) such that the closure holder is disposed at the proximal end (314), the distal end (312) is pivotally attached to an inner surface (116) of the outer tube distal end (114), the inner tube (100) when extended holds the flexible hinge (300) in a tension state, and the inner tube (100) when retracted causes the flexible hinge (300) to move to a memory state, g) a detachable closure device (120) disposed at the flexible hinge (300) closure holder (302), wherein the inner tube (100) is separable from the outer tube (110) to allow the flexible hinge (300) to move from a tension state to a memory state that allows the closure mechanism (120) to cover the vessel hole (150) and attach onto the outside of the vessel (210) in an enclosed position (124), wherein the closure device (120) is then detached from the flexible hinge closure holder (312) and the outer tube (110) is removed leaving the closure device (120) in an engaged position (126) to close the vessel opening (150), wherein the system (99) integrates the opening of the vessel (200) as well as closing the vessel opening (150).

44. The system of item 43, wherein the flexible hinge (300) is a memory wire.

45. The system of item 43, wherein the vessel (200) is an artery or a vein.

46. The system of item 43, wherein the closure device (120) is detached from the flexible hinge (300) closure holder (312) by a mechanical release, or electrolytic or thermal disconnection.

47. The system of item 43, wherein the closure device (120) comprises a metal clip, a hemostatic foam, a suture, a biodegradable patch, an adhesive gel, and/or a device or a substance that effectively covers, seals, or closes the hole (150) in the vessel (200) in a fail-safe manner that prevents re-opening of the vessel hole (150).

48. The system of item 43 further comprising a balloon inflation port (175) connected to a balloon inflation tube (176) integrated with the inner tube (100).

49. The system of item 48, wherein the inner tube (100) comprises a first lumen and a second lumen, wherein the first lumen is configured to have a medical device inserted therein, and wherein the second lumen is fluidly coupled to the balloon inflation port (175).

50. The system of item 49 further comprising an inflatable balloon (180) located at or near a distal end (104) of the inner tube (100) and fluidly coupled to the balloon inflation port (175) via the second lumen, wherein the balloon (180) is configured to be inflated locating the hole (150) in the vessel (200).

51. The system of item 49, wherein the medical device is a catheter, stent, balloon, therapeutic drug infusion, or wire.

52. The system of item 43, wherein a distal end of the inner tube (104) is radiodense for visibility under fluoroscopy or echogenic for visibility with ultrasound.

53. The system of item 43, wherein a distal end of the outer tube (114) is radiodense for visibility under fluoroscopy or echogenic for visibility with ultrasound.

54. The system of item 43, wherein the inner tube (100) further comprises a pressure monitoring sensor, a flow monitoring sensor, or both.

55. The system of item 43, wherein the outer tube (110) is equipped with a pressure monitoring sensor, a flow monitoring sensor, or both.

56. The system of item 43, wherein the outer tube (110) is configured so as to not enter into or puncture the vessel (200).

57. The system of item 56, wherein the outer tube (110) is configured to have a larger diameter than the inner tube (100), to be shorter than the inner tube (100), and/or has a blunt distal end (114).

58. The system of item 43, wherein more than one flexible hinge is pivotally attached to the inner surface of the distal end (114) of the outer tube (110).

59. A method for forming and closing a hole in a vessel, the method comprising a) providing an all-in-one device (99) comprising:
  i. an inner tube (100) comprising a first proximal end (102) and a first distal end (104);
  ii. an outer tube (110) that surrounds the inner tube (100), wherein the outer tube (110) comprises a second proximal end (112) and a second distal end (114); and
  iii. a closure mechanism (120) effectuated between a space (125) between the inner (100) and outer tube (110) and/or disposed along the distal end of the outer tube (114);

b) disposing the distal end of the inner tube (104) onto an outer surface of the vessel (210);

c) inserting the distal end of the inner tube (104) through the surface of the vessel (210), thereby forming a hole (150) in the vessel (200) and entering the vessel (200), wherein the distal end of the second tube (114) is disposed at or near the vessel hole (150) and does not enter the vessel (200);

d) withdrawing the distal end of the inner tube (104) from the vessel (200); wherein withdrawing the inner tube (100) releases the closure mechanism (120) onto the outer surface of the vessel (210), e) detaching the closure device (120) from the distal end of the outer tube (114); and f) removing the outer tube (110) leaving the closure device (120) to effectively close the vessel hole (150).

59. The method of item 58, wherein the vessel (200) is a blood vessel comprising an artery or a vein.

60. The method of item 58, the closure mechanism (120) is selected from a group consisting of metal clip, a hemostatic foam, a suture, a biodegradable patch, an adhesive gel. and a device or a substance that effectively covers, seals, or closes the hole (150) in the vessel (200) in a fail-safe manner that prevents re-opening of the hole (150).

61. The method of item 58 further comprising a balloon inflation port (175) integrated with the inner tube (100).

62. The method of item 61, wherein the inner tube (100) comprises a first lumen and a second lumen, wherein the first lumen is configured to have a medical device inserted therein, and wherein the second lumen is fluidly coupled to the balloon inflation port (175).

63. The method of item 62 further comprising an inflatable balloon (180) located at or near a distal end of the inner tube (104) and fluidly coupled to the balloon inflation port (175) via the second lumen, wherein the balloon (180) is configured to be inflated locating the hole (150) in the vessel (200).

64. The method of item 62, wherein the medical device is a catheter, stent, balloon, therapeutic drug infusion, or wire.

65. The method of item 58, wherein a distal end of the inner tube (104) is radiodense for visibility under fluoroscopy or echogenic for visibility with ultrasound.

66. The method of item 58, wherein a distal end of the outer tube (114) is radiodense for visibility under fluoroscopy or echogenic for visibility with ultrasound.

67. The method of item 58, wherein the inner tube (100) further comprises a pressure monitoring sensor, a flow monitoring sensor, or both.

68. The method of item 58, wherein the outer tube (110) is equipped with a pressure monitoring sensor, a flow monitoring sensor, or both.

69. The method of item 58, wherein the inner tube (100) is separable from the outer tube (110) to expose the closure device (120), wherein the closure device (120) is in a release position (122) to cover the vessel hole (150) and attach onto the outside of the vessel (200) in an enclosed position (124), wherein the closure device (120) is then detached from the outer tube (110) and the outer tube (110) is removed leaving the closure device (120) in an engaged position (126) to close the vessel hole (150).

70. The method of item 58, wherein prior to closing the hole (150), a medical device is inserted through the hole (150) via the inner tube (100) and into the vessel (200), wherein the medical device is selected from a group consisting of a catheter, stent, balloon, therapeutic drug infusions, and wire, 71. The method of item 58, wherein the outer tube (110) is shorter than the inner tube (100).

72. The system of item 58, wherein the outer tube (110) is configured as to not enter into or puncture the vessel (200).

73. The system of item 72, wherein the outer tube (110) is configured to have a larger diameter than the inner tube (100), to be shorter than the inner tube (100), and/or to have a blunt distal end (114).

74. A method for forming and closing a hole (150) in a vessel (200), the method comprising
a) providing an all-in-one device (199) comprising:
  i. an inner tube (100) comprising a first proximal end (102) and a first distal end (104);
  ii. an outer tube (110) that surrounds the inner tube (100), wherein the outer tube (110) comprises a second proximal end (112) and a second distal end (114);
  iii. a flexible hinge (300) positioned between the outer tube (110) and the inner tube (100), the flexible hinge (300) having a closure holder (302) and an arm (304), the arm (304) having a distal end (312) and a proximal end (314),
    wherein the closure holder (302) is disposed at a distal end (312) of the flexible hinge (300) and the flexible hinge (300) is pivotally attached to an inner surface of the second distal end (114), and
    wherein the inner tube (100) holds the flexible hinge (300) in a tension state;
  iv. a closure mechanism (120) disposed at the closure holder (302);
b) disposing the distal end of the inner tube (104) onto an outer surface of the vessel (200);
c) inserting the distal end of the inner tube (104) through the surface of the vessel (210), thereby forming a hole (150) in the vessel (200) and entering the vessel (200), wherein the distal end of the second tube (114) is disposed at or near the vessel hole (150) and does not enter the vessel (200);
d) withdrawing the distal end of the inner tube (104) from the vessel (200); wherein withdrawing the inner tube causes the flexible hinge (300) to move to a memory state, wherein moving to the memory state moves the closure mechanism (120) to the surface of the vessel (210),
e) detaching the closure device (120) from the distal end of the outer tube (114) by the force of the flexible hinge (300) moving from the tension state to the memory state; and
f) removing the outer tube (110) leaving the closure device (120) to effectively close the vessel hole (150).

75. The method of item 74, wherein the flexible hinge (300) is a memory wire.

76. The method of item 74, the closure mechanism (120) is selected from a group consisting of metal clip, a hemostatic foam, a suture, a biodegradable patch, an adhesive gel. and a device or a substance that effectively covers, seals, or closes the hole (150) in the vessel (200) in a fail-safe manner that prevents re-opening of the hole (150).

77. The method of item 74 further comprising a balloon inflation port (175) integrated with the inner tube (100).

78. The method of item 77, wherein the inner tube (100) comprises a first lumen and a second lumen, wherein the first lumen is configured to have a medical device inserted therein, and wherein the second lumen is fluidly coupled to the balloon inflation port (175).

79. The method of item 78 further comprising an inflatable balloon (180) located at or near a distal end of the inner tube (104) and fluidly coupled to the balloon inflation port (175) via the second lumen, wherein the balloon (180) is configured to be inflated locating the hole (150) in the vessel (200).

80. The method of item 78, wherein the medical device is a catheter, stent, balloon, therapeutic drug infusion, or wire.

81. The method of item 74, wherein a distal end of the inner tube (104) is radiodense for visibility under fluoroscopy or echogenic for visibility with ultrasound.

82. The method of item 74, wherein a distal end of the outer tube (114) is radiodense for visibility under fluoroscopy or echogenic for visibility with ultrasound.

83. The method of item 74, wherein the inner tube (100) further comprises a pressure monitoring sensor, a flow monitoring sensor, or both.

84. The method of item 74, wherein the outer tube (110) is equipped with a pressure monitoring sensor, a flow monitoring sensor, or both.

85. The method of item 74, wherein prior to closing the hole (150), a medical device is inserted through the hole (150) via the inner tube (100) and into the vessel (200), wherein the medical device is selected from a group consisting of a catheter, stent, balloon, therapeutic drug infusions, and wire, 86. The method of item 74, wherein the outer tube (110) is shorter than the inner tube (100).

87. The system of item 74, wherein the outer tube (110) is configured as to not enter into or puncture the vessel (200).

88. The system of item 87, wherein the outer tube (110) is configured to have a larger diameter than the inner tube (100), to be shorter than the inner tube (100), and/or to have a blunt distal end (114).

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A percutaneous blood vessel opening and closure system (199) comprising:
  a) an inner tube (100) comprising a proximal end (102) and a distal end (104), wherein the distal end (104) is inserted through the skin, disposed on the surface of the vessel (200), and creates an opening or hole (150) in a vessel (200) and enters the vessel (200) to provide percutaneous access and entry to the vessel (200);
  b) an outer tube (110) that surrounds the inner tube (100), wherein the outer tube (110) is positioned relative to the inner tube (100) so that the distal end of the outer tube (114) is disposed at or near the vessel opening or hole (150) and does not enter the vessel (200);
  c) a flexible hinge (300) having a closure holder (302) and an arm (304), the arm having a distal end (312) and a proximal end (314) such that the closure holder is disposed at the proximal end (314), the distal end (312) is pivotally attached to an inner surface (116) of the outer tube distal end (114), the inner tube (100) when extended holds the flexible hinge (300) in a tension state, and the inner tube (100) when retracted causes the flexible hinge (300) to move to a memory state,
  d) a detachable closure device (120) disposed at the flexible hinge (300) closure holder (302),
  wherein the inner tube (100) is separable from the outer tube (110) to allow the flexible hinge (300) to move from a tension state to a memory state that allows the closure mechanism (120) to cover the vessel hole (150) and attach onto the outside of the vessel (210) in an enclosed position (124), wherein the closure device (120) is then detached from the flexible hinge closure holder (312) and the outer tube (110) is removed leaving the closure device (120) in an engaged position (126) to close the vessel opening (150),
  wherein the system (99) integrates the opening of the vessel (200) as well as closing the vessel opening (150).

2. The system of claim 1, wherein the flexible hinge (300) is a memory wire.

3. The system of claim 1, wherein the vessel (200) is an artery or a vein.

4. The system of claim 1, wherein the closure device (120) is detached from the flexible hinge (300) closure holder (312) by a mechanical release, or electrolytic or thermal disconnection.

5. The system of claim 1, wherein the closure device (120) comprises a metal clip, a hemostatic foam, a suture, a biodegradable patch, an adhesive gel, and/or a device or a substance that effectively covers, seals, or closes the hole (150) in the vessel (200) in a fail-safe manner that prevents re-opening of the vessel hole (150).

6. The system of claim 1 further comprising a balloon inflation port (175) connected to a balloon inflation tube (176) integrated with the inner tube (100).

* * * * *